United States Patent [19]

Agarwal et al.

[11] Patent Number: 4,693,920

[45] Date of Patent: Sep. 15, 1987

[54] PRESSURE SENSITIVE COMPOSITE MATERIAL

[75] Inventors: Arun K. Agarwal, Woodbridge; Charles Balian, Guilford, both of Conn.

[73] Assignee: CHR Industries, Inc., New Haven, Conn.

[21] Appl. No.: 903,300

[22] Filed: Sep. 3, 1986

[51] Int. Cl.[4] .............. A61F 13/02

[52] U.S. Cl. .............. 428/40; 428/284; 428/285; 428/287; 428/337; 428/343; 428/354; 428/355; 428/914

[58] Field of Search .............. 428/40, 284, 285, 287, 428/343, 354, 355, 914

[56] References Cited

U.S. PATENT DOCUMENTS

| | | | |
|---|---|---|---|
| 4,146,635 | 3/1979 | Eigenmann | 418/354 |
| 4,264,388 | 4/1981 | McClintock | 428/354 |
| 4,359,502 | 11/1981 | Caponigro et al. | 428/354 |
| 4,374,883 | 2/1983 | Winslow | 428/354 |
| 4,511,621 | 4/1985 | Thomas et al. | 428/354 |
| 4,599,265 | 7/1986 | Esmay | 428/354 |
| 4,614,677 | 9/1986 | Pennace et al. | 428/354 |

FOREIGN PATENT DOCUMENTS

| | | | |
|---|---|---|---|
| 0143380 | 9/1982 | Japan | 428/354 |

*Primary Examiner*—James J. Bell

*Attorney, Agent, or Firm*—DeLio & Associates

[57] ABSTRACT

A flame retardant, solvent fuels and lubricating fluids resistant, non-flagging, printable, pressure sensitive laminate material capable of service up to 260° C., comprising, a non-woven substrate, an adhesive coating on one side of said substrate and a resin coating on the other side of said substrate.

8 Claims, 2 Drawing Figures

PRESSURE SENSITIVE COMPOSITE MATERIAL

Figure 1:
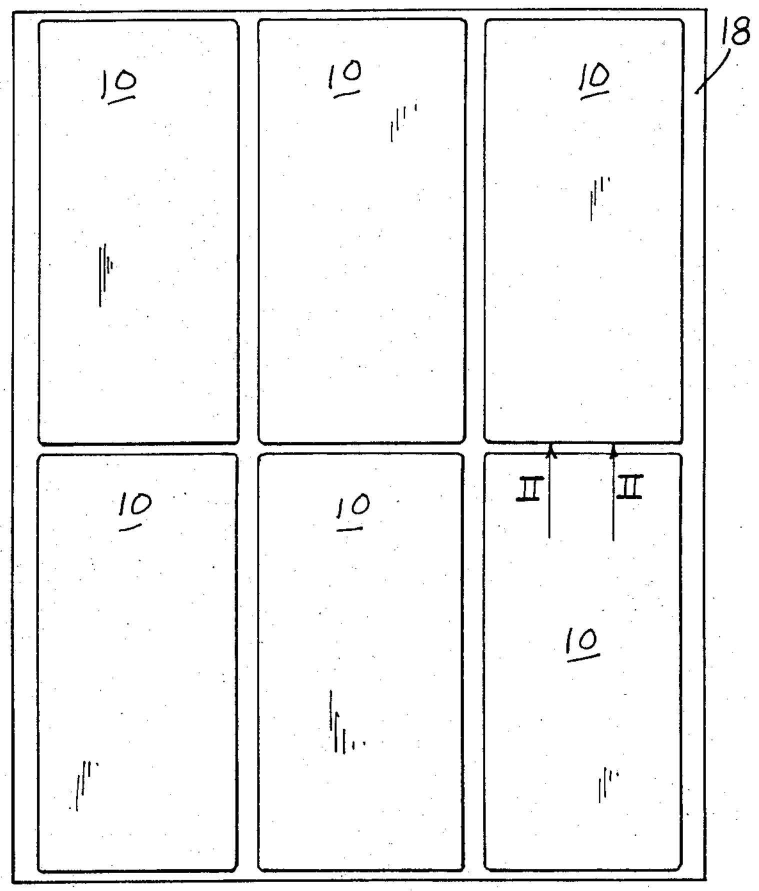

This invention relates to a pressure sensitive composite material and more particularly to a flame retardant, printable, solvent, fuels and lubricating fluids resistant, material for use at elevated temperatures.

The material of the present invention is adapted particularly for use in aircraft and ships as an identification tape/label in various applications such as electrical wiring identification, hydraulic line identification, etc. In these applications the tape/label is usually wrapped around electrical wire bundles or hydraulic lines which may be exposed to hydraulic line fluids, oils, greases, fuels, and the like.

There has been a growing need for materials which are resistant to attack from petroleum based products such as oils, greases, hydraulic fluids, jet engine fuels, ethylene and propylene glycol and the like. These tape/label materials must be able to meet high performance standards under different environmental conditions. As such, a tape or label material must be flame retardant so that it is self-extinguishing when flame is removed from it. The material must also be pressure sensitive and self-adhesive as well as having good adhesive properties to other materials. In addition, such material must be capable of reliable service up to 260° C. while being solvent, fuels and lubricating fluids resistant. Upon meeting all of these requirements, the material must also be capable of being printed upon by impact and laser marking machines. All of these requirements must be contained in a material which in many instances is no more than 1 mm thick.

In responding to these requirements, the prior art has attempted to meet the needs of the industry with the use of polyvinylfluorides, polytetrafluoroethylenes and polyimide materials. For the most part, these prior art materials in various forms do not meet all the high performance standards as set forth above and as required by the industry. To begin with, most of the prior art materials are not capable of use up to 260° C. Many of them are not flame-retardant because they are combustible after the flame has been removed. In other instances, the prior art materials are not solvent fuels and lubricating fuels resistant. In many instances the materials that have been used in the prior art are not capable of being printed upon by impact or non-impact printing methods such as laser marking machines and the like.

Heretofore, in the prior art, the balance between printable materials and solvent, fluids and lubricating fluids resistant materials has always required a compromise. When one material was highly printable it was not solvent, fuels and lubricating fluids resistant. When the material was solvent, fuels and lubricating fluids resistant, it was not capable of being printed upon. Since the materials for these particular tape/label applications must meet both of these requirements, the prior art materials were deficient.

In view of the foregoing, one of the objects of the present invention is to provide a new and improved pressure sensitive composite material for use under particular environmental conditons.

Another object of the present invention is to provide a new and improved pressure sensitive composite material for use in temperatures up to 260° C., at which temperatures the material is solvent, fuels and lubricating fluids resistant, non-flagging and flame retardant, while at the same time being printable by impact and non-impact printing methods.

Still other objects and advantages of the invention will be apparent from the following specification. The invention accordingly comprises a product possessing the features, properties and the relation of components which will be exemplified in the product hereinafter described. The scope of the invention will be indicated in the claims.

For full understanding of the invention, reference is had to the following description.

Figure 2:
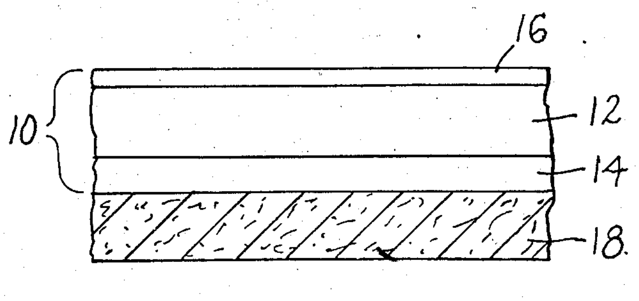

A practical embodiment of the invention is shown, somewhat diagrammatically, in the accompanying drawing wherein:

FIG. 1 is a plan view of a release liner on which are mounted a plurality of labels made from the pressure sensitive composite material of the instant invention, and FIG. 2 is a section taken on line II—II of FIG. 1.

The product, 10, of the instant invention, is composed of three principal components, a substrate 12, an adhesive coating 14 and a resin coating 16. The substrate 12 is usually of thicknesses less than 1 mm and preferably in the range of 0.025 mm to about 0.25 mm. This substrate is made up of a, non-woven polyamide, however a non-woven fiberglass mat may also be used as the substrate material.

The adhesive coating or layer 14 is placed on the surface of one side of the substrate. This adhesive layer must be capable of performing under the extreme conditions of high temperature and still be solvent, fuels and lubricating fluids resistant. To this end, it is contemplated that the adhesive coating layer 14 will be a polyacrylate and it will be applied to one side of the substrate 12. In addition to the polyacrylates, polysiloxanes, polyurethanes and resin modified natural and synthetic rubbers can be used. The resin modified natural and synthetic rubbers are carefully chosen so that they have the desired adhesive properties, but they are principally chosen from the group consisting of the styrene-butadiene polymers, polyisoprene, polychloroprene and butadiene-acrylonitrile polymers. The adhesive coating is applied to one side of the substrate by appropriate coating methods and apparatus and they may be applied separately or simultaneously with the resin coating 16 which is put on the surface of the other side of the substrate material 12, that is, the side opposite the adhesive coating side.

The resin coating 16 must be compatible with the substrate material and the adhesive layer while being capable of meeting the stringent, high performance requirements in service, that it be solvent, fluids and lubricating fluids resistant, capable of service up to 260° C. in relatively thin sections, of below 1 mm in thickness, and at the same time be capable of being printed upon by impact and laser printing methods. This resin coating 16 is chosen from the polyacrylates, polyesters, polyurethanes and butadiene-acrylonitrile polymers. The resin can also be chosen from solvent resistant resins such as polychloroprene and the chlorosulfonated-polyethylenes.

The thickness of the adhesive coating 14 is preferably between 0.01 mm to about 0.10 mm while the resin coating 16, preferably ranges in thickness from about 0.001 mm to about 0.075 mm. The adhesive chosen for use as the adhesive coating may be partially cross-linked by appropriate chemical and/or ionizing radiation cross linking techniques. To enhance the solvent resistance, etc., the resins that are chosen for use as the top coating can be either the curable types of resin or the non-curable types. A blending of curable and non-curable resins may be used to obtain the optimum balance of properties. In any event, the curable resins may be partially cross-linked either chemically or by ionizing radiation.

Release liner material 18 is calendered paper and the like and is applied to the adhesive coating layer 14 thus facilitating the peel off of the composite material 10 when it is manufactured in sheet and roll form. The release liner can be of considerable thickness compared to the composite material 10.

If the material 10 needs to be color coded, the resin 16 can be provided with an appropriate color pigment which will be compatible with the resin coating chosen for the particular use. In any event, it is the product 10 composed of the substrate 12, the adhesive coating 14 and the resin coating 16, which results in the unique properties of the composite material.

Examples of laminate materials prepared in accordance with the teachings of this invention to meet the requirements noted above are as follows:

The following resin solutions were prepared for use in the instant invention:

| | A | B | C |
|---|---|---|---|
| Acryloid B-84 | 25 gr | 15 gr | — |
| Acryloid B-44S | — | — | 15 gr |
| Acryloid AT-51 | — | 8 gr | — |
| UCD 5680 N | — | — | 15 gr |
| CP-2360 | — | 10 gr | — |
| Toluene | 35 gr | 35 gr | 35 gr |

NOTES:

1. Acryloid is a trade name of Rohm and Haas Company for their family of acrylic resins.
2. UCD 5680 D is Bee Chemical Company's product number for red cadmium based pigment dispersion.
3. CP-2360 is Ferro Corporation's product number for red cadmium based pigment. This must be pre-dispersed in a solvent such as toluene and a wetting agent. This dispersion is made by using a high speed mixer.

Solution A is an example of a clear, uncured coating.

Solution B is an example of a red colored, partially cured coating.

Solution C is an example of a yellow colored uncured coating.

EXAMPLE #1

A 0.05 mm polyamide paper (Nomex Aramid Paper Type 410) was coated on one side with solution "A" using an applicator roller and doctoring off excess with wire-wound Meyer Rod.

The coated polyamide paper was dried in a conventional air circulating oven. The coating of the resin was 0.01 mm when dry. The polyamide paper was then coated on the other side with a polyacrylate adhesive (H & N Chemical Company's Polyad 130). The adhesive was applied with a reverse roll coater and deposited at 0.04 mm dry thickness. The adhesive was dried and cured and the completed composite was then wound up against a 60# silicone coated release paper.

Testing showed this composite to have excellent printability and good solvent, fuels and lubricating fluids resistance and good printability.

EXAMPLE #2

Example #2 was prepared in the same manner as example #1 except that the resin solution B was used.

The dry thickness for both the resin and adhesive were the same as in example #1.

Testing showed this composite to have excellent solvent, fluids and lubricating fluids resistance printability.

EXAMPLE #3

Example #3 was prepared in the same manner as example #1 except a 0.075 mm Nomex polyamide paper was used and Solution C was used.

Testing showed an excellent balance of printability and solvent fuels and lubricating fluids resistance.

All examples (1, 2 and 3) were stable and useful up to 260° C. Although none of adhesive coatings or adhesives were flame retardant per se, all laminates passed the flame retardant requirements.

It will thus be seen that the objects set forth above among those made apparent from the preceeding description can be efficiently attained and since certain changes may be made in the above product without departing from the spirit and scope of the invention, it is intended that all matter contained in the above description shall be interpreted as illustrative and not of limiting sense. It is also to be understood that the following claims are intended to cover all of the generic and specific features of the invention herein described. Particularly it is to be understood that in the claims set forth below, ingredients or compounds recited in the singular are intended to include compatible mixtures of such ingredients wherever the sense permits.

What is claimed is:

1. A composite material comprising, a non-woven substrate chosen from the group consisting of polyamide and fiberglass mat, an adhesive coating applied to the surface of one side of said substrate, said adhesive coating chosen from the group of pressure sensitive adhesives consisting of polyacrylates, polysiloxanes, polyurethanes and resin modified natural and synthetic rubbers such as styrene-butadiene polymers, polyisoprene, polychloroprene, butadiene-acrylonitrile polymers, and a resin coating applied to the surface of the other side of the substrate, said resin coating chosen from the group consisting of polyacrylates, polyesters, polyurethanes, butadiene-acrylonitrile polymers, and solvent resistant resins such as polychloroprene and chlorosulfonated-polyethylenes.

2. The material of claim 1 further defined in that the adhesive coating is at least partially cross-linked.

3. The material of claim 1 further defined in that the substrate ranges in thickness from about 0.025 mm to about 0.25 mm, the adhesive coating ranges in thickness from about 0.01 mm to about 0.10 mm and the resin coating ranges in thickness from about 0.001 mm to about 0.075 mm.

4. The material of claim 3, further defined in that the adhesive coating is at least partially cross-linked.

5. The material of claim 1 further defined in that the product is provided with a release liner which is placed over the adhesive coating.

6. The material of claim 1 wherein said composite material comprises a laminated adhesive tape which is printable on the resin coated side.

7. The material of claim 6 wherein said non-woven substrate consists essentially of polyamide.

8. The material of claim 6 wherein said non-woven substrate consists essentially of fiberglass.

* * * * *